(12) United States Patent
Chou et al.

(10) Patent No.: US 8,470,026 B2
(45) Date of Patent: Jun. 25, 2013

(54) MECHANICAL HEART VALVE APPARATUS

(75) Inventors: Chau-Chang Chou, Taichung (TW); Te-Chun Wu, Keelung (TW)

(73) Assignee: National Taiwan Ocean University, Keelung (TW)

( * ) Notice: Subject to any disclaimer, the term of this patent is extended or adjusted under 35 U.S.C. 154(b) by 154 days.

(21) Appl. No.: 13/103,413

(22) Filed: May 9, 2011

(65) Prior Publication Data

US 2012/0101573 A1 Apr. 26, 2012

(30) Foreign Application Priority Data

Oct. 26, 2010 (TW) .............................. 99136484 A

(51) Int. Cl.
  *A61F 2/24* (2006.01)
(52) U.S. Cl.
  CPC .................................... *A61F 2/2403* (2013.01)
  USPC ....................................... 623/2.28; 623/2.32
(58) Field of Classification Search
  USPC ................................................. 623/2.2–2.34
  See application file for complete search history.

(56) References Cited

U.S. PATENT DOCUMENTS

| | | | | |
|---|---|---|---|---|
| 2,877,792 | A * | 3/1959 | Tybus | 137/512.1 |
| 4,078,268 | A | 3/1978 | Possis | |
| 4,178,639 | A | 12/1979 | Bokros | |
| 4,328,592 | A * | 5/1982 | Klawitter | 623/2.32 |
| 4,774,981 | A * | 10/1988 | Mizusawa | 137/512.1 |
| 5,108,425 | A * | 4/1992 | Hwang | 623/2.26 |
| 5,116,366 | A * | 5/1992 | Hwang | 623/2.26 |
| 5,123,920 | A * | 6/1992 | Bokros | 623/2.26 |
| 5,236,451 | A * | 8/1993 | Bokros et al. | 623/2.32 |
| 5,607,469 | A * | 3/1997 | Frey | 623/2.21 |
| 6,723,123 | B1 * | 4/2004 | Kazatchkov et al. | 623/2.2 |
| 7,992,563 | B2 * | 8/2011 | Doshi | 128/207.14 |

* cited by examiner

*Primary Examiner* — Thomas J Sweet
*Assistant Examiner* — Cheryl Miller
(74) *Attorney, Agent, or Firm* — The Webb Law Firm

(57) ABSTRACT

A mechanical heart valve apparatus includes a loop-shaped frame defining a valve opening and formed with a pair of transverse slot units and a pair of longitudinal slots; and a pair of valve plates mounted on the loop-shaped frame. Each of the valve plates includes a pair of first studs that are slidably and respectively inserted into the transverse slot units, and a second stud that is slidably inserted into a respective one of the longitudinal slots. The valve plates are pivoted to each other so as to be rotatable relative to each other between a closed position, in which the second studs are disposed adjacent to upper ends of the longitudinal slots, and an opening position, in which the second studs are disposed adjacent to lower ends of the longitudinal slots.

4 Claims, 3 Drawing Sheets

US 8,470,026 B2

MECHANICAL HEART VALVE APPARATUS

CROSS-REFERENCE TO RELATED APPLICATION

This application claims priority of Taiwanese Application No. 099136484, filed on Oct. 26, 2010.

BACKGROUND OF THE INVENTION

1. Field of the Invention

This invention relates to a mechanical heart valve apparatus, more particularly to a mechanical heart valve apparatus having a valve opening and two valve plates synchronously rotatable about a pivot axis for closing and opening the valve opening.

2. Description of the Related Art

U.S. Pat. Nos. 4,078,268 and 4,178,639 disclose conventional mechanical heart valves that include a loop-shaped frame defining a valve opening, and valve plates independently pivoted to the loop-shaped frame for closing and opening the valve opening. The valve plates can be pushed to open by a positive pressure from the blood flow. However, the valve plates may be subjected to different positive pressures from the blood flow, which results in different degrees of opening of the valve plates, respectively. As a consequence, the blood flow cannot smoothly pass through the valve opening, which can result in intermittent regurgitation and increase the working burden on the heart and the chances of damaging the valve plates and hemolysis.

SUMMARY OF THE INVENTION

Therefore, the object of the present invention is to provide a mechanical heart valve apparatus that can overcome the aforesaid drawbacks associated with the prior art.

According to the present invention, there is provided a mechanical heart valve apparatus that comprises: a loop-shaped frame defining a valve opening and formed with a pair of transverse slot units and a pair of longitudinal slots, the transverse slot units being opposite to each other in a first direction, each of the transverse slot units extending in a second direction along a corresponding transverse axis, each of the longitudinal slots extending in a third direction along a corresponding longitudinal axis transverse to and intersecting the transverse axis of a corresponding one of said transverse slot units, and having opposite upper and lower ends; and a pair of valve plates mounted movably on the loop-shaped frame and operable for closing and opening the valve opening. Each of the valve plates includes a pair of first studs that are slidably and respectively inserted into the transverse slot units and a second stud that is slidably inserted into a respective one of the longitudinal slots. The valve plates are pivoted to each other so as to be rotatable relative to each other about a pivot axis parallel to the first direction between a closed position, in which the valve plates close the valve opening, the second studs of the valve plates are respectively disposed adjacent to the upper ends of the longitudinal slots, and the first studs of one of the valve plates are disposed distal from the first studs of the other of the valve plates, and an opening position, in which the valve plates open the valve opening, the second studs are respectively disposed adjacent to the lower ends of the longitudinal slots, and the first studs of one of the valve plates are disposed adjacent to the first studs of the other of the valve plates.

BRIEF DESCRIPTION OF THE DRAWINGS

In drawings which illustrate an embodiment of the invention.

DETAILED DESCRIPTION OF THE PREFERRED EMBODIMENT

Figure 1:
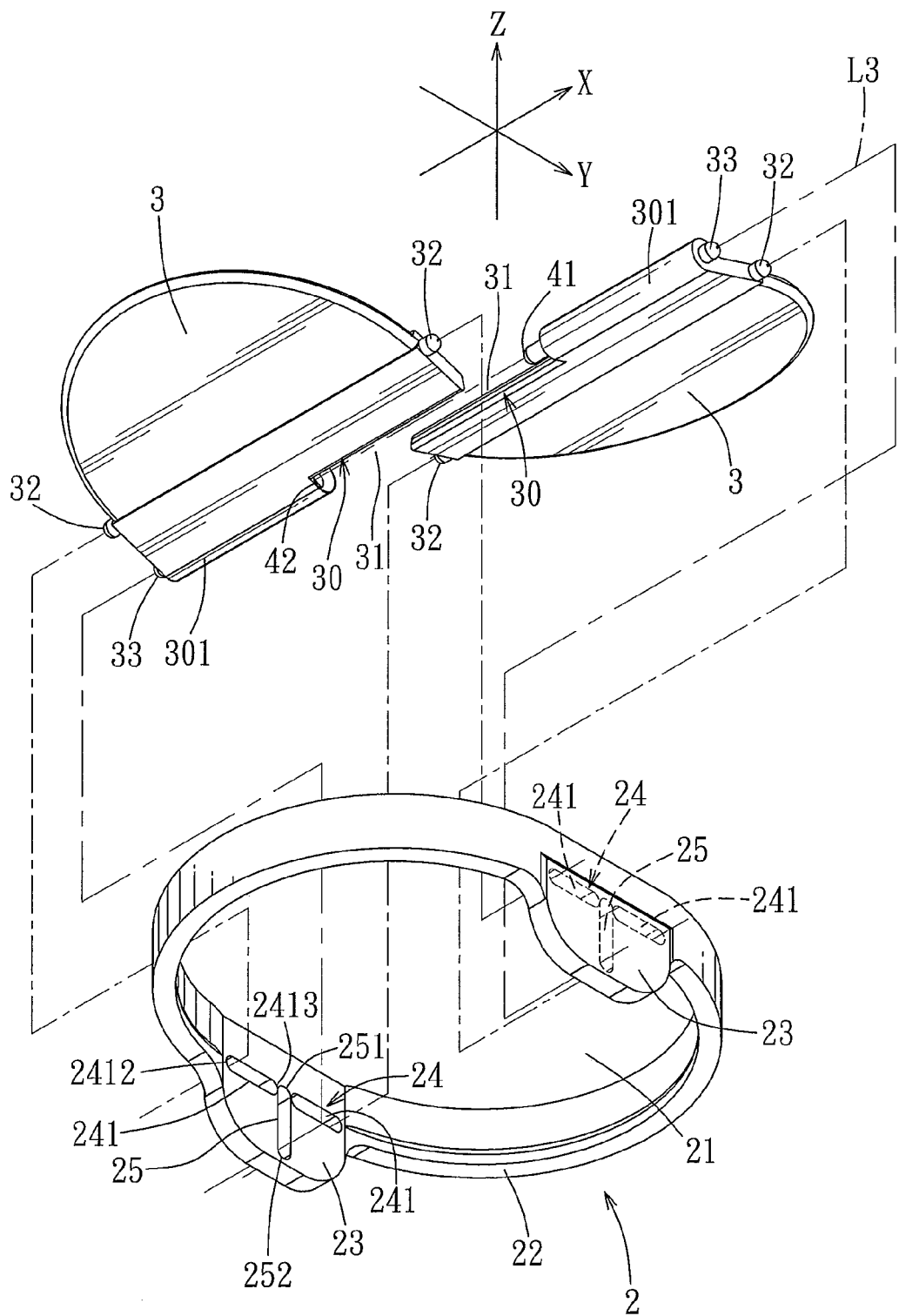
FIG. 1 is an exploded perspective view of the preferred embodiment of a mechanical heart valve apparatus according to this invention.
Figure 2:
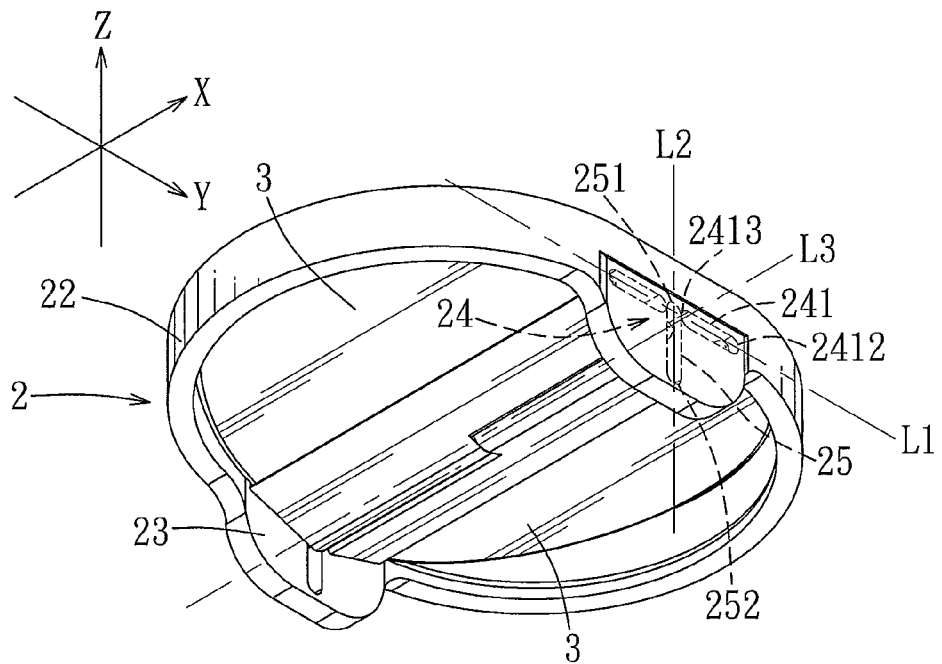
FIG. 2 is an assembled perspective view of the preferred embodiment, illustrating a state where a pair of valve plates are disposed at a closed position.
Figure 3:
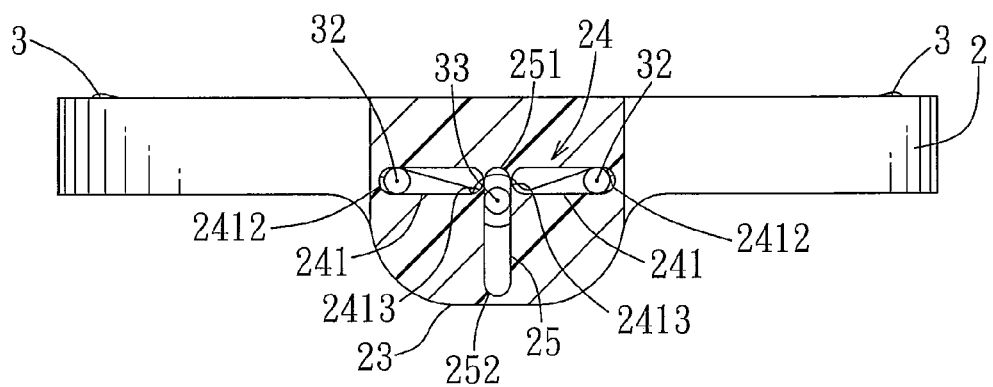
FIG. 3 is a partly sectional view of the preferred embodiment to illustrate the state where the valve plates are disposed at the closed position.
Figure 4:
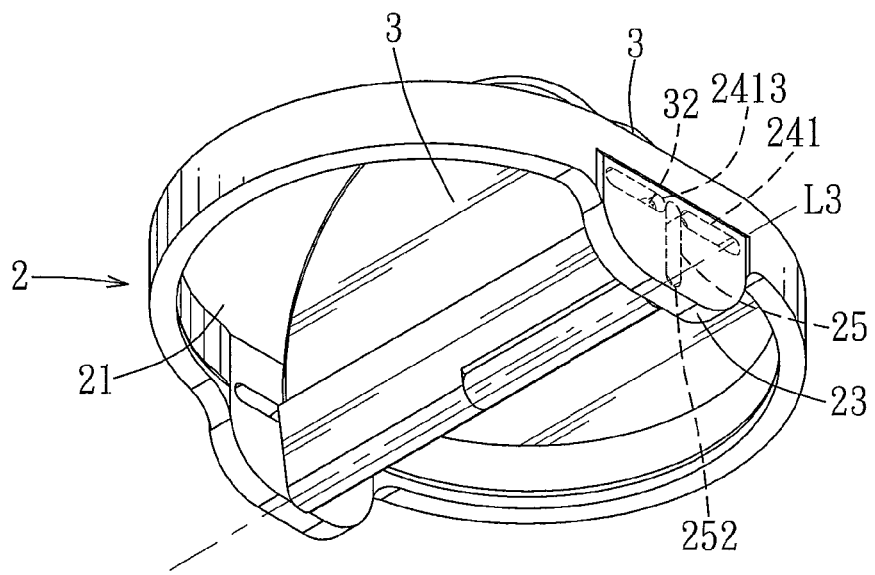
FIG. 4 is a perspective view of the preferred embodiment, illustrating a state where the valve plates are disposed at an opening position.
Figure 5:
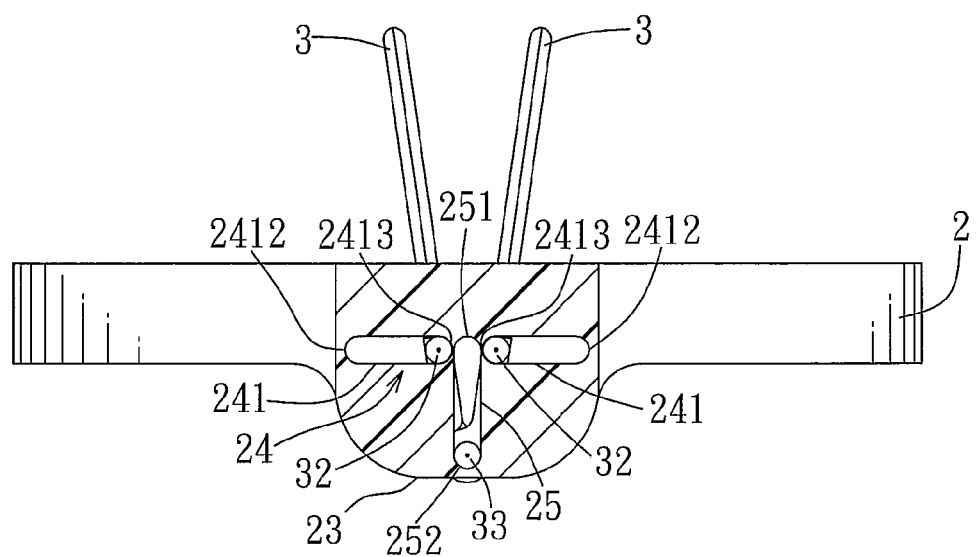
FIG. 5 is a partly sectional view of the preferred embodiment to illustrate the state where the valve plates are disposed at the opening position.

Referring to FIGS. 1 to 5, the preferred embodiment of a mechanical heart valve apparatus according to the present invention is shown to include: a loop-shaped frame 2 defining a valve opening 21 and formed with a pair of transverse slot units 24 and a pair of longitudinal slots 25, the transverse slot units 24 being opposite to each other in a first direction (X), each of the transverse slot units 24 extending in a second direction (Y) along a corresponding transverse axis (L1), each of the longitudinal slots 25 extending in a third direction (Z) along a corresponding longitudinal axis (L2) transverse to and intersecting the transverse axis (L1) of a corresponding one of the transverse slot units 24, and having opposite upper and lower ends 251, 252; and a pair of valve plates 3 mounted movably on the loop-shaped frame 2 and operable for closing and opening the valve opening 21. Each of the valve plates 3 includes a pair of first studs 32 that are slidably and respectively inserted into the transverse slot units 24 and a second stud 33 that is slidably inserted into a respective one of the longitudinal slots 25. The valve plates 3 are pivoted to each other so as to be rotatable relative to each other about a pivot axis (L3) parallel to the first direction (X) between a closed position (see FIGS. 2 and 3), in which the valve plates 3 close the valve opening 21, the second studs 33 of the valve plates 3 are respectively disposed adjacent to the upper ends 251 of the longitudinal slots 25, and the first studs 32 of one of the valve plates 3 are disposed distal from the first studs 32 of the other of the valve plates 3, and an opening position (see FIGS. 4 and 5), in which the valve plates 3 open the valve opening 21, the second studs 33 are respectively disposed adjacent to the lower ends 252 of the longitudinal slots 25, and the first studs 32 of one of the valve plates 3 are disposed adjacent to the first studs 32 of the other of the valve plates 3.

In this embodiment, each of the transverse slot units 24 has a pair of transverse slots 241 that extend and that are aligned in the second direction (Y). Each of the transverse slots 241 of each of the transverse slot units 24 has opposite first and second ends 2412, 2413. The first ends 2412 of the transverse slots 241 of each of the transverse slot units 24 are disposed distal from each other, while the second ends 2413 of the transverse slots 241 of each of the transverse slot units 24 are disposed adjacent to each other. The first studs 32 of the valve plates 3 are respectively disposed at the first ends 2412 of the transverse slots 241 of the transverse slot units 24 when the valve plates 3 are disposed at the closed position. The first studs 32 of the valve plates 3 are respectively disposed adjacent to the second ends 2413 of the transverse slots 241 of the transverse slot units 24 when the valve plates 3 are disposed at the opening position. Alternatively, this embodiment may be modified in such a manner such that the transverse slots 241 of each of the transverse slot units 24 are joined in an end-to-end manner to form a long single slot.

The loop-shaped frame 2 includes a loop-shaped base portion 22 and a pair of protruding portions 23 protruding from the base portion 22 in the third direction (Z), parallel to each other, and aligned along the first direction (X). Each of the protruding portions 23 is formed with a respective one of the transverse slot units 24 and a respective one of the longitudinal slots 25.

Each of the valve plates 3 has an L-shaped side wall 30 that defines a recess 31 and that has an engaging portion 301. The engaging portion 301 of the L-shaped side wall 30 of each of the valve plates 3 is received in the recess 31 defined by the L-shaped side wall 30 of the other of the valve plates 3. The engaging portions 301 of the L-shaped side walls 30 of the valve plates 3 are pivoted to each other. In this embodiment, the L-shaped side wall 30 of one of the valve plates 3 is formed with a pivot stud 41 protruding therefrom and defining the pivot axis (L3), while the L-shaped side wall 30 of the other of the valve plates 3 is formed with a pivot hole 42 for receiving pivotally the pivot stud 41 therein, thereby permitting relative rotation between the valve plates 3 about the pivot axis (L3).

In operation, when the valve plates 3 are disposed at the closed position and are pushed by a positive pressure from a blood flow to rotate synchronously relative to the loop-shaped frame 2 about the pivot axis (L3), the second studs 33 of the valve plates 3 will move along the third direction (Z) from the upper ends 251 of the longitudinal slots 25 toward the lower ends 252 of the longitudinal slots 25, and the first studs 32 of the valve plates 3 will move along the second direction (Y) from the first ends 2412 of the transverse slots 241 of the transverse slot units 24 toward the second ends 2413 of the transverse slots 241 of the transverse slot units 24, thereby disposing the valve plates 3 at the opening position. When the valve plates 3 are disposed at the opening position and are pushed by gravity or a negative pressure from a blood flow, the second studs 33 of the valve plates 3 will move along the third direction (Z) from the lower ends 252 of the longitudinal slots 25 toward the upper ends 251 of the longitudinal slots 25, and the first studs 32 of the valve plates 3 will move along the second direction (Y) from the second ends 2413 of the transverse slots 241 of the transverse slot units 24 toward the first ends 2412 of the transverse slots 241 of the transverse slot units 24, thereby disposing the valve plates 3 at the closed position.

When the valve plates 3 are subjected to different positive or negative pressures from the blood flow to rotate about the pivot axis (L3), due to the engagement between the pivot stud 41 and the pivot hole 42, the engaging portion 301 of the L-shaped side wall 30 of one of the valve plates 3 which is subjected to a higher pressure can drag the engaging portion 301 of the L-shaped side wall 30 of the other of the valve plates 3 which is subjected to a lower pressure to concurrently move downwardly or upwardly, thereby permitting synchronous rotation of the valve plates 3 for achieving a smooth blood flow through the valve opening 21 so as to reduce occurrences of intermittent regurgitation and hemolysis and the working burden on the heart, and to enhance the service life of the mechanical heart valve apparatus.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A mechanical heart valve apparatus comprising:
   a loop-shaped frame defining a valve opening and formed with a pair of transverse slot units and a pair of longitudinal slots, said transverse slot units being opposite to each other in a first direction, each of said transverse slot units extending in a second direction along a corresponding transverse axis, each of said longitudinal slots extending in a third direction along a corresponding longitudinal axis transverse to and intersecting the transverse axis of a corresponding one of said transverse slot units, and having opposite upper and lower ends; and
   a pair of valve plates mounted movably on said loop-shaped frame and operable for closing and opening said valve opening, each of said valve plates including a pair of first studs that are slidably and respectively inserted into said transverse slot units and a second stud that is slidably inserted into a respective one of said longitudinal slots, said valve plates being pivoted to each other so as to be rotatable relative to each other about a pivot axis parallel to the first direction between a closed position, in which said valve plates close said valve opening, said second studs of said valve plates are respectively disposed adjacent to said upper ends of said longitudinal slots, and said first studs of one of said valve plates are disposed distal from said first studs of an other of said valve plates, and an opening position, in which said valve plates open said valve opening, said second studs are respectively disposed adjacent to said lower ends of said longitudinal slots, and said first studs of one of said valve plates are disposed adjacent to said first studs of an other of said valve plates;
   wherein each of said transverse slot units has a pair of transverse slots that extend and that are aligned in the second direction, each of said transverse slots of each of said transverse slot units having opposite first and second ends, said first ends of said transverse slots of each of said transverse slot units being disposed distal from each other, said second ends of said transverse slots of each of said transverse slot units being disposed adjacent to each other, said first studs of said valve plates being respectively disposed at said first ends of said transverse slots of said transverse slot units when said valve plates are disposed at the closed position, said first studs of said valve plates being respectively disposed at said second ends of said transverse slots of said transverse slot units when said valve plates are disposed at the opening position.

2. The mechanical heart valve apparatus of claim 1, wherein said loop-shaped frame includes a loop-shaped base portion and a pair of protruding portions protruding from said base portion in the third direction, parallel to each other, and aligned along the first direction, each of said protruding portions being formed with a respective one of said transverse slot units and a respective one of said longitudinal slots.

3. The mechanical heart valve apparatus of claim 1, wherein each of said valve plates has an L-shaped side wall that defines a recess and that has an engaging portion, said engaging portion of said L-shaped side wall of each of said valve plates being received in said recess defined by said L-shaped side wall of an other of said valve plates, said engaging portions of said L-shaped side walls of said valve plates being pivoted to each other.

4. The mechanical heart valve apparatus of claim 3, wherein said L-shaped side wall of one of said valve plates is formed with a pivot stud protruding therefrom and defining said pivot axis, said L-shaped side wall of an other of said valve plates being formed with a pivot hole for receiving pivotally said pivot stud therein.

* * * * *